US008420063B2

(12) United States Patent
Ikeda et al.

(10) Patent No.: US 8,420,063 B2
(45) Date of Patent: Apr. 16, 2013

(54) LIP COSMETICS

(75) Inventors: Tomoko Ikeda, Yokohama (JP); Tomo Osawa, Yokohama (JP); Noriko Tomita, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 13/258,474

(22) PCT Filed: Mar. 30, 2010

(86) PCT No.: PCT/JP2010/055716
§ 371 (c)(1),
(2), (4) Date: Sep. 22, 2011

(87) PCT Pub. No.: WO2010/113956
PCT Pub. Date: Oct. 7, 2010

(65) Prior Publication Data
US 2012/0014895 A1 Jan. 19, 2012

(30) Foreign Application Priority Data

Mar. 31, 2009 (JP) ................................. 2009-085229
Dec. 11, 2009 (JP) ................................. 2009-281566

(51) Int. Cl.
*A61Q 1/04* (2006.01)
*A61K 8/00* (2006.01)

(52) U.S. Cl.
USPC ........................................................ 424/64

(58) Field of Classification Search .................... 424/64, 424/401
See application file for complete search history.

(56) References Cited

U.S. PATENT DOCUMENTS

| 5,085,856 A * | 2/1992 | Dunphy et al. ................. 424/64 |
| 5,672,339 A | 9/1997 | Soyama et al. |
| 5,725,845 A | 3/1998 | Krog et al. |
| 5,945,092 A | 8/1999 | Krog et al. |
| 6,482,398 B1 | 11/2002 | Rabe et al. |
| 2001/0031269 A1 | 10/2001 | Arnaud |
| 2004/0151680 A1* | 8/2004 | Patil et al. ................... 424/70.12 |
| 2006/0110347 A1* | 5/2006 | Lu et al. ........................ 424/70.1 |
| 2011/0097289 A1* | 4/2011 | Viala et al. ....................... 424/63 |

FOREIGN PATENT DOCUMENTS

| JP | 9-48709 | 2/1997 |
| JP | 10-72315 | 3/1998 |
| JP | 2000-53530 | 2/2000 |
| JP | 2000-204016 | 7/2000 |
| JP | 2001-39817 | 2/2001 |
| JP | 2001-199846 | 7/2001 |
| JP | 2002-255827 | 9/2002 |
| JP | 2005-314366 | 11/2005 |
| JP | 2006-282592 | 10/2006 |
| JP | 2007-238578 | 9/2007 |
| JP | 2008-247804 | 10/2008 |
| JP | 2009-73797 | 4/2009 |
| WO | 96/40044 | 12/1996 |
| WO | 97/16157 | 5/1997 |

OTHER PUBLICATIONS

Japanese Patent Abstract for Publication No. 2000-053530 published Feb. 22, 2000, ten pages.
Japanese Patent Abstract for Publication No. 2002-255827 published Sep. 11, 2002, nine pages.
Japanese Patent Abstract for Publication No. 2000-204016 published Jul. 25, 2000, seven pages.
Japanese Patent Abstract for Publication No. 2006-282592 published Oct. 19, 2006, six pages.
Notification of Transmittal of Translation of the International Preliminary Report on Patentability, Written Opinion of the International Searching Authority; International Application No. PCT/JP2010/055716; Mailing date: Nov. 24, 2011, International Filing Date: Mar. 30, 2010; Applicant: Shiseido Company Ltd.—five pages.
Japanese Patent Abstract for Publication No. 2005-314366 published Nov. 10, 2005, 35 pages.
Japanese Patent Abstract for Publication No. 10-072315 published Mar. 17, 1998, six pages.
Japanese Patent Abstract for Publication No. 2001-039817 published Feb. 13, 2001, ten pages.
Japanese Patent Abstract for Publication No. 2008-247804 published Oct. 16, 2008, 12 pages.
Japanese Patent Abstract for Publication No. 2007-238578 published Sep. 20, 2007, 13 pages.
Japanese Patent Abstract for Publication No. 2009-073797 published Apr. 9, 2009, 12 pages.

* cited by examiner

*Primary Examiner* — Gina C Justice
(74) *Attorney, Agent, or Firm* — Rankin, Hill & Clark LLP

(57) ABSTRACT

The present invention provides a lip cosmetic that has good gloss and good stability, while maintaining post-application secondary adhesion resistance. The lip cosmetic of the present invention is characterized by comprising the following components (a) to (d):
(a) 4.5 to 35 mass % of glyceryl monoisostearate;
(b) 20 to 80 mass % of one or more kinds of methyl phenyl silicones that do not separate out when mixed with (a) at 90° C. and separate out when mixed with (a) at 25° C.;
(c) 5 mass % or more of water and/or glycerin, relative to the component (a), and 24 mass % or less, relative to the total amount of the cosmetic; and
(d) 4 to 10 mass % of a wax.

20 Claims, 2 Drawing Sheets

Test Example 1　　Test Example 2　　Test Example 3　　Test Example 4

LIP COSMETICS

RELATED APPLICATIONS

This application claims the priority of Japanese Patent Application No. 2009-85229 filed on Mar. 31, 2009 and Japanese Patent Application No. 2009-281566 filed on Dec. 11, 2009, which are incorporated herein by reference.

FIELD OF THE INVENTION

The present invention relates to a lip cosmetic, and in particular, relates to a lip cosmetic having excellent secondary adhesion resistance, excellent gloss durability, and good stability.

BACKGROUND OF THE INVENTION

Conventional lip cosmetic have presented the problem of secondary adhesion, namely a lipstick is transferred onto a site contacted by a lip (for example, a cup) after the lipstick is applied to the lip. By contrast, lipstick compositions having so-called secondary adhesion resistance effect that causes little secondary adhesion have been developed.

For example, Patent Document 1 discloses a transfer-resistant cosmetic composition comprising: a volatile hydrocarbon solvent; a non-volatile silicone compound that can be dissolved or dispersed in the volatile hydrocarbon solvent; and non-volatile hydrocarbon oil that is dissolved in the volatile solvent and is incompatible with the non-volatile silicone compound, wherein the non-volatile hydrocarbon oil has a certain solubility parameter.

However, this transfer-resistant cosmetic composition has room for improvement in stability. Due to its large amount of wax, the feeling in use in a liquid state cannot be obtained, and also gloss is insufficient.

Patent Document 2 discloses a lipstick composition having transfer resistance, comprising perfluoropolyether-type non-volatile oil and volatile oil, which are incompatible with each other. In this Patent Literature 2, oils are separated during application to a support to move onto a first composition.

However, the first composition is in a solid state due to a considerable amount of wax. Thus, a sufficient gloss or moisture cannot be obtained. Moreover, for this system, the incompatible oil phases are difficult to favorably disperse, resulting in the problem of stability against sweating etc.

Patent Document 3 discloses a stick cosmetic having transfer resistance, comprising volatile oil and a silicone surfactant, wherein pigments are favorably dispersed.

However, this stick cosmetic has a large proportion of the volatile oil in the composition and thus has the disadvantage that its matte finish tends to provide a feeling of dryness on lips.

Patent Document 4 discloses a one-phase composition for lipsticks, comprising volatile oil and a silicone resin.

However, after evaporation of the volatile oil, this composition for lipsticks tends to cause a feeling of dryness over time, although it has improved transfer resistance. Moreover, a film of the resin remains on lips. The composition further has the following disadvantages that; it causes a filmy feeling and tightness, and the obtained adhesion is matte.

Patent Document 5 discloses an oil-in-oil emulsion composition comprising: continuous-phase oil comprising a silicone coating agent, volatile silicone oil, non-volatile silicone liquid oil, and an emulsifying agent; and dispersion-phase oil comprising ester oil and a coloring material, wherein the blending quantities of the continuous-phase oil and the dispersion-phase oil are at a dispersion-phase oil/(dispersion-phase oil and continuous-phase oil) ratio of 0.05 to 0.5.

However, this oil-in-oil emulsion composition tends to generate color unevenness due to the presence of the coloring material in the dispersion phase. Furthermore, for this system, temporal stability may be difficult to maintain.

Patent literature 1: Japanese unexamined patent publication No. 2001-199846
Patent literature 2: International unexamined patent publication No. 96/40044
Patent literature 3: International unexamined patent publication No. 97/16157
Patent literature 4: Japanese unexamined patent publication No. H9-48709
Patent literature 5: Japanese unexamined patent publication No. 2000-53530

DISCLOSURE OF THE INVENTION

Problem to be Solved by the Invention

The present invention was made in view of the above-described conventional art. An object of the invention is to provide a lip cosmetic that has excellent secondary adhesion resistance, excellent gloss durability after application, and excellent stability.

Means to Solve the Problem

The present inventors have diligently studied; as a result, the present inventors have found that a lip cosmetic having, after application, both secondary adhesion resistance and a gloss can be obtained by blending a specific surfactant, water and/or glycerin, a specific silicone oil, and a wax.

That is, the lip cosmetic of the present invention is characterized by comprising the following components (a) to (d):
(a) 4.5 to 35 mass % of glyceryl monoisostearate;
(b) 20 to 80 mass % of one or more kinds of methyl phenyl silicones that do not separate out when mixed with (a) at 90° C. and separate out when mixed with (a) at 25° C.;
(c) 5 mass % or more of water and/or glycerin, relative to the component (a), and 24 mass % or less, relative to the total amount of the cosmetic; and
(d) 4 to 10 mass % of a wax.

In the lip cosmetic of the present invention, it is preferable that component (b) contains trimethyl pentaphenyl trisiloxane.

In the lip cosmetic, it is preferable that 50 mass % or more of trimethyl pentaphenyl trisiloxane is contained in the component (b).

In the lip cosmetic, it is preferable that neither glyceryl diisostearate nor glyceryl triisostearate is contained. If contained, it is preferable that only 10 mass % or less, relative to the total amount of the cosmetic, is contained in total.

In the lip cosmetic, it is preferable that (e) 1 to 20 mass % of a coloring material is contained.

Effect of the Invention

A lip cosmetic having good gloss and good stability, while maintaining post-application secondary adhesion resistance, can be obtained by blending the specific amounts of (a) glyceryl monoisostearate, (b) one or more kinds of methyl phenyl silicones that do not separate out when mixed with (a) at 90° C. and separate out when mixed with (a) at 25° C., (c) water and/or glycerin, and (d) a wax.

BEST MODE FOR CARRYING OUT THE INVENTION

Figure 1:
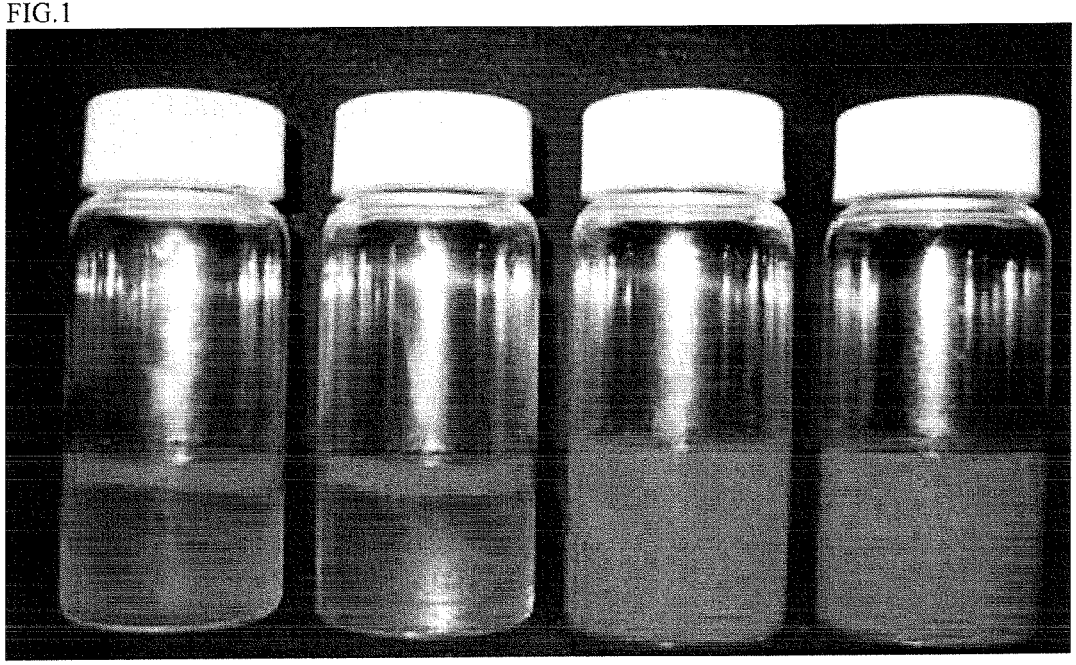
FIG. 1 shows the test results for the phase separation state of glyceryl monoisostearate, various oils, coloring material, and water.

Generally, if the secondary adhesion resistance effect is high, the gloss upon application has a tendency to be lacking. On the other hand, the base having a gloss has a drawback in that the secondary adhesion easily takes place because there is plenty residual oil. In the present invention, by blending a specific surfactant and non-compatible silicone oil therewith, the silicone oil separates into the surface layer on the lip upon application, and a gloss is provided. Because the surfactant, in the inner layer, holds in the coloring material, the secondary adhesion is difficult to take place. As a result, a lip cosmetic without secondary adhesion and with an excellent gloss can be obtained.

In the following, each component is described in detail.

((a) Glyceryl Monoisostearate)

Glyceryl monoisostearate, which is component (a) used in the present invention, can be obtained by various known synthesis methods. According to a common synthesis method, it is formed as a mixture of glyceryl monoisostearate, glyceryl diisostearate, and glyceryl triisostearate. A molecular distillation method is generally used as a method for purifying glyceryl monoisostearate, however, the present invention is not limited thereto.

Purity of glyceryl monoisostearate can be measured with a common method such as gas chromatography (GC), gel permeation chromatography (GPC), and high-performance liquid chromatography (HPLC). It is preferable for the formation of liquid crystals that the isostearyl group of glyceryl monoisostearate is the one wherein the main component is, in particular, a methyl group branched chain.

The blending quantity of component (a) in the present invention is 4.5 to 35 mass % relative to the total amount of the cosmetic and preferably 7 to 30 mass %. If the blending quantity of component (a) is too small, the secondary adhesion resistance effect may be inferior. If the blending quantity of component (a) is too large, the secondary adhesion resistance effect may be inferior because the amount of component (b) becomes relatively small. In addition, there is a trend that stickiness appears after application.

Here, the blending quantity of glyceryl monoisostearate does not include glyceryl diisostearate, glyceryl triisostearate, glycerin, isostearic acid, and the like, which are contained as impurities, and it means the mass that is actually blended. In the present invention, the sum of the blending quantities of glyceryl diisostearate and glyceryl triisostearate is preferably 10 mass % or less, relative to the total amount of the cosmetic, especially preferably 7 mass % or less, and more preferably that they are not contained. When the blending quantities of glyceryl diisostearate and glyceryl triisostearate are large, the formation of liquid crystals becomes difficult; therefore, the secondary adhesion resistance effect tends to be inferior.

((b) Methyl Phenyl Silicone)

In the present invention, component (b) will separate from component (a), after application, and form the surface layer; thus the secondary adhesion resistance effect is achieved and the gloss is improved.

In the present invention, component (b) is one or more kinds of methyl phenyl silicones that do not separate out when mixed with (a) at 90° C. and separate out when mixed with (a) at 25° C., and the methyl phenyl silicone can be one kind or a mixture of two or more kinds.

Here, the presence or absence of "separation" was measured under the following conditions.

(Measurement Condition)

A mixture of (a) and decamethylcyclopentasiloxane (1:1 mass ratio) was prepared. This mixture was used in the ratio (mixture:(b)=1:2 (mass ratio)) and mixed with stirring at 90° C. The mixture was allowed to stand at room temperature (25° C.). When the boundary was uniformly separated into two layers, it was denoted "separated". When it was a translucent state or a transparently miscible state without a boundary, it was denoted "not separated".

As described above, it is necessary that component (b), which is blended in the lip cosmetic of the present invention, does not separate out when mixed with component (a) at 90° C. When this condition is not satisfied, the production cannot be achieved. It is also preferable that component (b), which is blended in the lip cosmetic of the present invention, does not separate out when mixed with component (a) at 70° C.

It is also necessary that component (b) separates out when mixed with component (a) at 25° C. When this condition is not satisfied, the formation of liquid crystals becomes difficult, and the secondary adhesion resistance effect may be inferior.

Trimethyl pentaphenyl trisiloxane and diphenyl dimethicone are preferable as the methyl phenyl silicone used in the present invention. It is especially preferable that trimethyl pentaphenyl trisiloxane is contained. When a mixture thereof is used, it suffices if they are blended in the proportion so that the above-described condition is met as a whole mixture. It is more preferable that 50 mass % or more of trimethyl pentaphenyl trisiloxane is contained in methyl phenyl silicones.

As a commercial trimethyl pentaphenyl trisiloxane, methyl phenyl silicone FZ3156 (165 mm$^2$/s (25° C.), manufactured by Dow Corning Toray Co., Ltd.) can be listed. As a commercial diphenyl dimethicone, silicone KF54 (400 mm$^2$/s (25° C.), manufactured by Shin-Etsu Chemical Co., Ltd.), silicone KF50-300CS (manufactured by Shin-Etsu Chemical Co., Ltd.), silicone KF-54HV (manufactured by Shin-Etsu Chemical Co., Ltd.), and the like can be listed.

As components (b) of the present invention, as well the above, diphenylsiloxyphenyl trimethicone (for example, silicone KF56 (14 mm$^2$/s (25° C.), manufactured by Shin-Etsu Chemical Co., Ltd.)), phenyl trimethicone (for example, silicone SH556 (22 mm$^2$/s (25° C.), manufactured by Dow Corning Toray Co., Ltd.)), and the like can be used.

In particular, when diphenylsiloxyphenyl trimethicone is used, there is an effect in that the gloss improves upon application.

The blending quantity of component (b) is 20 to 80 mass % relative to the total amount of the cosmetic, preferably 30 to 80 mass %, and more preferably 45 to 70 mass %. If the blending quantity of component (b) is less than 20 mass %, the secondary adhesion easily takes place and there is a little gross. If the blending quantity of component (b) exceeds 80 mass %, the stability is poor.

((c) Water and/or Glycerin)

In the present invention, water and/or glycerin, which is component (c), is blended 5 mass % or more and preferably 20 mass % or more relative to component (a), and 24 mass % or less and preferably 18 mass % or less relative to the total amount of the cosmetic.

If the blending quantity of component (c) is less than 5 mass % relative to component (a), the necessary amount for the formation of liquid crystals cannot be reached, and the secondary adhesion resistance effect is inferior. If the blending quantity of component (c) becomes large relative to the total amount of the cosmetic, vertical wrinkles become noticeable. Therefore, the blending quantity of component (c) is 24 mass % or less relative to the total amount of the cosmetic and preferably 18 mass % or less.

((d) Wax)

Wax used in the present invention is not limited in particular as long as it can be normally blended for cosmetics. For example, polyethylene wax, rice wax, carnauba wax, candelilla wax, beeswax, ceresin, microcrystalline wax, solid paraffin, Japan wax, and the like can be listed.

Wax, which is component (d), is 4 to 10 mass % relative to the total amount of the cosmetic and preferably 6 to 9 mass %.

If the blending quantity of component (d) is less than 4 mass %, the solidification is difficult. If the blending quantity exceeds 10 mass %, the spreadability becomes heavy and the gloss is lost.

((e) Coloring Material)

In the present invention, it is preferable to blend a coloring material normally used in lip cosmetics.

Such coloring materials can be powdery or lake-like (oil-containing state) so far as they are coloring materials normally used in lipsticks. They can be inorganic pigments, organic pigments, or pearlescent agents. The coloring material blended in the present invention is preferably a hydrophobized coloring material.

The coloring material has a higher affinity to (a) glyceryl monoisostearate than to oil (especially (b) methyl phenyl silicones). Therefore, the coloring material is held in component (a) (present near component (a)). On the lip, the coloring material is present in the inner layer, which is located in the inner side of component (b); thus the secondary adhesion is difficult to take place.

If a coloring material is blended, the blending quantity is 1 to 20 mass % relative to the total amount of the cosmetic, and preferably 3 to 15 mass %.

A film-forming agent can be additionally blended in the lip cosmetic of the present invention.

Examples of film-forming agents include (alkyl acrylate/dimethicone) copolymer etc. Specifically, Silicone KP545 (manufactured by Shin-Etsu Chemical Co., Ltd.) is commercially available.

When a film-forming agent is blended, the blending quantity is preferably 2 to 15 mass % relative to the total amount of the cosmetic, and more preferably 5 to 10 mass %.

It is preferable that the lip cosmetic of the present invention is constituted so that the separation does not take place throughout the entire production process and the state of one homogeneous phase is maintained. More specifically, it is preferable that the lip cosmetic is constituted so that the entire composition does not separate at 90° C. and the state of one homogeneous phase is maintained.

In the lip cosmetic of the present invention, in addition to the above-described essential components, the components normally used in lip cosmetics (for example, oil other than the above-described oils, powder, polymer compound, moisturizer, perfume, antioxidant agent, preservative, and beauty component) can be blended so far as the effect of the present invention is not undermined.

For example, an oil component other than component (b) can also be blended in the present invention. As such an oil component, it is especially preferable to blend a volatile oil. As volatile oils, volatile hydrocarbon oils and volatile silicone oils can be listed. For example, if 0.5 to 25 mass % of decamethylcyclopentasiloxane, relative to the total amount of the cosmetic, is blended, the stability is further improved.

As moisturizers, for example, polyol moisturizers such as propylene glycol and 1,3-butylene glycol can be listed.

The lip cosmetic of the present invention can be applied to lipsticks, lip glosses, lip bases, overcoats for lipsticks, lip creams, and the like.

EXAMPLES

The present invention will be further described in the following examples. However, the invention is not limited by these examples. Unless otherwise specified, the blending quantity of each component will be expressed in mass %.

Prior to illustrating the examples, the methods for the evaluation tests used in the present invention will be explained.

(1) Evaluation Test of the Separation State of (a) and (b)

The separation state of (a) and (b) (or silicone oil) was measured under the following conditions. If the separation did not take place at 90° C. and the separation took place at 25° C., it was denoted "A" and others were denoted "C".

(Measurement Condition)

A Mixture of (a) and decamethylcyclopentasiloxane (1:1 mass ratio) was prepared. This mixture was used in the ratio (mixture:(b)=1:2 (mass ratio)) and mixed with stirring at 90° C. The mixture was allowed to stand at room temperature (25° C.). When the boundary was uniformly separated into two layers, it was denoted "separated". When it was a translucent state or a transparently miscible state without a boundary, it was denoted "not separated".

(2) Evaluation Test of the Secondary Adhesion Resistance Effect

The actual usability test by 10 professional panelists was carried out. The five-level sensory evaluation (scoring) of the secondary adhesion resistance effect was based on the below-described scoring criteria. The determination was by the score average value based on the below-described evaluation criteria.

(Score)
5 points: very excellent
4 points: excellent
3 points: ordinary
2 points: poor
1 point: very poor (Evaluation Criteria)
S: The score average value is 4.5 point or higher and less than 5 points.
A*: The score average value is 4 point or higher and less than 4.5 points.
A: The score average value is 3.5 point or higher and less than 4 points.
B: The score average value is 2.5 point or higher and less than 3.5 points.
C: The score average value is 1 point or higher and less than 2.5 points.

The examples listed with "-" in the table had poor stability, and the secondary adhesion resistance effect could not be measured.

(3) Evaluation Test of the Stability

The wax uniformity of the cutting plane of the stick-shaped sample was evaluated based on the below-described evaluation criteria.

(Evaluation Criteria)
A*: uniform
A: almost uniform
B: almost non-uniform
C: non-uniform Examples 1 to 17, Comparative Examples 1 to 11, and Reference Example Lipsticks were prepared, by the normal method, according to the formulations shown in the following Tables 1 to 6, and they were evaluated based on the above-described criteria. The results are shown in Tables 1 to 6. Glyceryl monoisostearate was produced by the normal method, and the actual amount was calculated from the amount of the purified one with a purity of 98%.

In the examples and reference examples in Tables 3, 4, and 6, the evaluation results for the separation state of (a) and (b) were all "A".

TABLE 1

|   |   | Example 1 | Comparative Example 1 | Comparative Example 2 | Comparative Example 3 | Comparative Example 4 | Example 2 |
|---|---|---|---|---|---|---|---|
| (a) | Glyceryl monoisostearate | 14 | 14 | 14 | 14 | 14 | 14 |
| (b) | Trimethyl pentaphenyl trisiloxane (viscosity: 165 mPa·s) ※1 | 71 | — | — | — | — | 40 |
|   | Diphenyl dimethicone (viscosity: 400 mPa·s) ※2 | — | 71 | — | — | — | 30 |
|   | Diphenylsiloxyphenyl trimethicone (viscosity: 14 mPa·s) ※3 | — | — | 71 | — | — | — |
|   | Dimethylpolysiloxane 100cs | — | — | — | 71 | — | — |
|   | Dimethylpolysiloxane 6cs | — | — | — | — | 71 | — |
|   | Coloring material | 4 | 4 | 4 | 4 | 4 | 5 |
| (d) | Polyethylene wax | 7 | 7 | 7 | 7 | 7 | — |
|   | Rice wax | — | — | — | — | — | 7 |
| (c) | Ion-exchanged water | 3 | 3 | 3 | 3 | 3 | 3 |
|   | Dynamite glycerin | 1 | 1 | 1 | 1 | 1 | 1 |
| (1) | Separation state of (a) and (b) | A | C | C | C | C | A |
| (2) | Secondary adhesion resistance effect | A* | — | C | — | — | A* |
| (3) | Stability | A | C | A* | C | C | A* |

※1: Methyl phenyl silicone FZ3156 (manufactured by Dow Corning Toray Co., Ltd.)
※2: Silicone KF54 (manufactured by Shin-Etsu Chemical Co., Ltd.)
※3: Silicone KF56 (manufactured by Shin-Etsu Chemical Co., Ltd.)

According to Table 1, the samples of Examples 1 and 2; wherein glyceryl monoisostearate, wax, water, and glycerin were contained, and a methyl phenyl silicone that does not separate out when mixed with glyceryl monoisostearate at 90° C. and separates out when mixed with glyceryl monoisostearate at 25° C. was blended; had excellent stability, and the secondary adhesion resistance effect was also excellent.

However, in Comparative Examples 1 and 2; wherein glyceryl monoisostearate, wax, water, and glycerin were contained, but a methyl phenyl silicone that does not satisfy the separation condition was contained; and in Comparative Examples 3 and 4; wherein other silicone oils were contained, the sample stability or the secondary adhesion resistance effect was inferior.

Accordingly, it is necessary to satisfy the condition that the (b) methyl phenyl silicone blended in the present invention does not separate out when mixed with (a) glyceryl monoisostearate at 90° C. and separates out when mixed with (a) glyceryl monoisostearate at 25° C. When this condition is satisfied, the secondary adhesion resistance effect may be achieved, liquid crystals may be formed, and the stability of the composition may be improved.

In order to verify the importance of the above-described separation condition in the selection of oil, the samples of the blending compositions, wherein various oils are blended, shown in the below Table 2 were produced. Respective samples were obtained by mixing glyceryl monoisostearate, various oils, and a coloring material at 90° C., adding warmed ion-exchanged water, and then centrifuging at 3000 rpm at room temperature for 30 minutes. The results are shown in Table 2 and FIG. 1.

TABLE 2

|   | Test Example 1 | Test Example 2 | Test Example 3 | Test Example 4 |
|---|---|---|---|---|
| Glyceryl monoisostearate | 8.82 | 8.82 | 8.82 | 8.82 |
| Trimethyl pentaphenyl trisiloxane (viscosity: 165 mPa·s) ※1 | 88.3 | — | — | — |
| Diphenyl dimethicone (viscosity: 400 mPa·s) ※2 | — | 88.3 | — | — |
| Diisostearyl malate (viscosity: 1600~2200 mPa·s) ※4 | — | — | 88.3 | — |
| Polyglyceryl-2 triisostearate (viscosity: 350 mPa·s) ※5 | — | — | — | 88.3 |
| Coloring material | 0.88 | 0.88 | 0.88 | 0.88 |
| Ion-exchanged water | 2 | 2 | 2 | 2 |
| (1) Separation state of (a) and (b) | A | A | C | C |

※4 Cosmol 222 (manufactured by The Nisshin OilliO Group, Ltd.)
※5 Cosmol 43 (manufactured by The Nisshin OilliO Group, Ltd.)

According to Table 2 and FIG. 1, the samples of Test Examples 1 and 2, which contain a methyl phenyl silicone that satisfies the separation condition of the present invention, separated into two layers. The coloring material was held in glyceryl monoisostearate of the upper layer.

On the other hand, the samples of Test Examples 3 and 4, which contain an oil that does not satisfy the separation condition of the present invention, did not separate. The coloring material was scattered in the sample.

Accordingly, when a methyl phenyl silicone that satisfies the separation condition of the present invention is blended, the separation into two layers takes place and the coloring material is held in glyceryl isostearate. Thus, the coloring material stays in the inner layer upon application on the lip, and the methyl phenyl silicone stays in the outer layer. As a result, a lip cosmetic excellent in the secondary adhesion resistance effect can be obtained.

TABLE 3

| | | Comparative Example 5 | Comparative Example 6 | Example 3 | Example 4 | Example 5 | Comparative Example 7 | Comparative Example 8 | Comparative Example 9 | Example 6 |
|---|---|---|---|---|---|---|---|---|---|---|
| (a) | Glyceryl monoisostearate | 2 | 2 | 5 | 30 | 35 | 40 | 40 | 50 | 14 |
| (b) | Trimethyl pentaphenyl trisiloxane (viscosity: 165 mPa·s) ※1 | 71.4 | 69.33 | 65.1 | 35.8 | 32.4 | 23.6 | 18.4 | 20 | — |
| | Diphenyl dimethicone (viscosity: 400 mPa·s) ※2 | — | — | — | — | — | — | — | — | 41 |
| | Diphenylsiloxyphenyl trimethicone (viscosity: 14 mPa·s) ※3 | — | — | — | — | — | — | — | — | 13 |
| | Decamethylcyclopentasiloxane | 15 | 15 | 15 | 15 | 6 | 15 | 15 | 6 | 15 |
| | Coloring material | 4 | 4 | 4 | 4 | 4 | 4 | 4 | 4 | 4 |
| (d) | Polyethylene wax | 7 | 7 | 7 | 7 | 7 | 7 | 7 | 7 | 7 |
| (c) | Ion-exchanged water | 0.5 | 2 | 3 | 6.3 | 12 | 8 | 12 | 10 | 4 |
| | Dynamite glycerin | 0.1 | 0.67 | 0.9 | 1.9 | 3.6 | 2.4 | 3.6 | 3 | 2 |
| (2) Secondary adhesion resistance effect | | C | C | A* | A | A | C | C | C | A* |
| (3) Stability | | A* | A* | A* | A* | A* | A* | A* | A* | A |

The samples of Examples 3 to 6, wherein glyceryl monoisostearate was suitably contained, were excellent in the secondary adhesion resistance effect and in stability.

On the other hand, in Comparative Examples 5 and 6, wherein the blending quantity of glyceryl monoisostearate was small, and in Comparative Examples 7 to 9, wherein the blending quantity was large, no lip cosmetics having a satisfactory secondary adhesion resistance effect could be obtained.

Thus, it is necessary that the lip cosmetic of the present invention contains 4.5 to 35 mass % of component (a) relative to the total amount of the cosmetic.

water and/or glycerin in order to form liquid crystals and provide the secondary adhesion resistance effect. Furthermore, it has become clear that the blending quantity needs to be 5 mass % or more relative to component (a) and 24 mass % or less relative to the total amount of the cosmetic.

Subsequently, in order to verify the formation of liquid crystals, the measurement was carried out with an X-ray small angle scattering (SAXS) measurement apparatus for the system of (a) glyceryl monoisostearate and (c) water and/or glycerin. The samples used in this test were obtained by mixing component (a) and component (c) in a ratio of 9:1

TABLE 4

| | Comparative Example 10 | Example 7 | Example 8 | Example 9 | Example 10 | Example 11 | Example 12 | Example 13 |
|---|---|---|---|---|---|---|---|---|
| Glyceryl monoisostearate | 14 | 14 | 14 | 14 | 14 | 14 | 14 | 14 |
| Trimethyl pentaphenyl trisiloxane (viscosity: 165 mPa·s) ※1 | 56 | 56 | 56 | 56 | 56 | 56 | 47 | 40 |
| Decamethylcyclopentasiloxane | 19 | 15 | 15 | 15 | 15 | 15 | 12 | 11 |
| Coloring material | 4 | 4 | 4 | 4 | 4 | 4 | 4 | 4 |
| Polyethylene wax | 7 | 7 | 7 | 7 | 7 | 7 | 7 | 7 |
| Ion-exchanged water | — | 1 | 4 | — | 3 | 2 | 12 | 18 |
| Dynamite glycerin | — | 0.3 | — | 4 | 1 | 2 | 4 | 6 |
| (2) Secondary adhesion resistance effect | B | A | A* | A* | A* | A* | A* | A* |
| (3) Stability | A* | A* | A* | A* | A* | A* | A* | A* |

According to Table 4, the sample of Comparative Example 10, wherein ion-exchanged water and dynamite glycerin were not blended, had a poor secondary adhesion resistance effect.

However, when the blending quantity of water and/or glycerin was increased, samples excellent in the secondary adhesion resistance effect could be obtained.

As a result of these investigations by the present inventors, the lip cosmetic of the present invention needs to contain (c)

at 90° C., allowing to cool to room temperature, and then carrying out centrifugal separation. The results are shown in FIG. 2.

Figure 2:
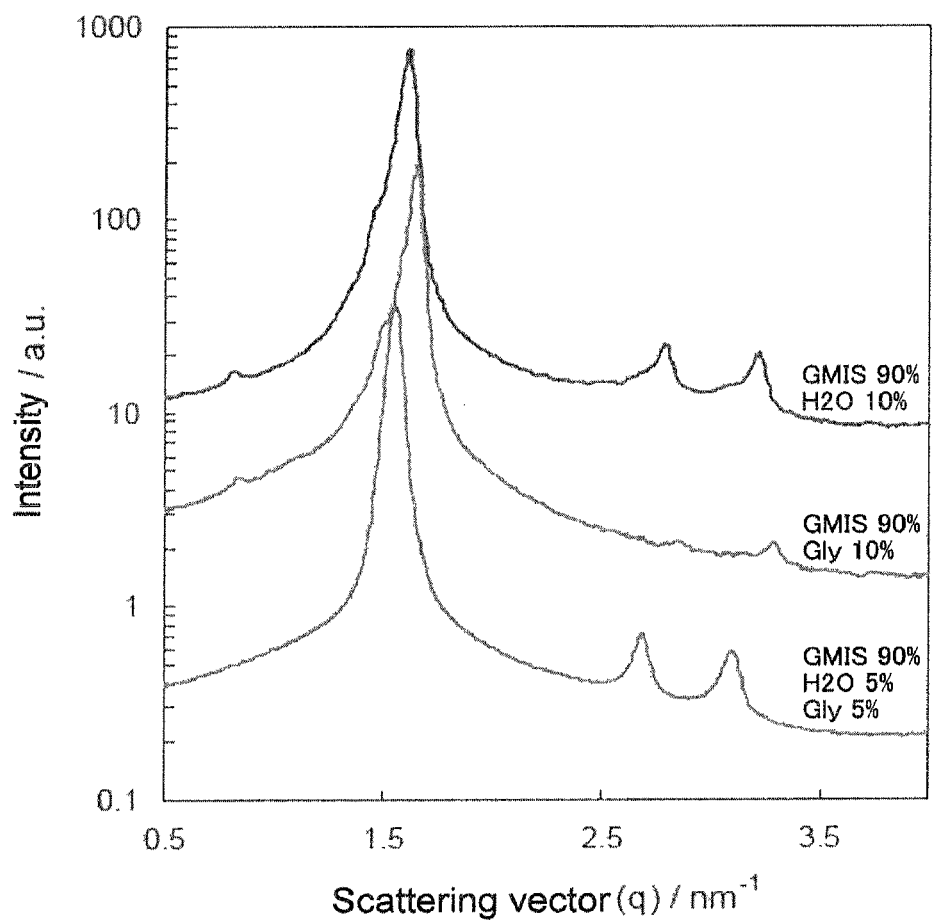
FIG. 2 shows the measurement results of X-ray small angle scattering for (a) glyceryl monoisostearate (GMIS) and (c) water (H2O) and/or glycerin (Gly) ((a):(c)=9:1).

As shown in FIG. 2, three sharp scattering peaks were observed. The ratio of the peak values was peculiar to that of reverse hexagonal liquid crystals. Thus, it was clarified that reverse hexagonal liquid crystals were formed.

TABLE 5

| | Example 1 | Example 11 | Example 12 | Example 13 | Example 14 | Comparative Example 11 |
|---|---|---|---|---|---|---|
| Glyceryl monoisostearate | 14 | 14 | 14 | 14 | 14 | 14 |
| Trimethyl pentaphenyl trisiloxane (viscosity: 165 mPa·s) ※1 | 71 | 56 | 34 | 20 | 28 | 11 |

TABLE 5-continued

|  | Example 1 | Example 11 | Example 12 | Example 13 | Example 14 | Comparative Example 11 |
|---|---|---|---|---|---|---|
| Diphenyl dimethicone (viscosity: 400 mPa · s) ※2 | — | — | 22 | 16 | 28 | 45 |
| Decamethylcyclopentasiloxane | — | 15 | 15 | 21 | 15 | 15 |
| Coloring material | 4 | 4 | 4 | 4 | 4 | 4 |
| Polyethylene wax | 7 | 7 | 7 | 7 | 7 | 7 |
| Ion-exchanged water | 3 | 3 | 3 | 6 | 3 | 3 |
| Dynamite glycerin | 1 | 1 | 1 | 2 | 1 | 1 |
| (1) Separation state of (a) and (b) | A | A | A | A | A | C |
| (2) Secondary adhesion resistance effect | A* | A* | A* | A | A | — |
| (3) Stability | A | A* | A* | A* | A* | C |

According to Example 11, when a portion of the methyl phenyl silicone in Example 1 was replaced by decamethylcyclopentasiloxane, the stability of the sample was improved.

Furthermore, the percentages of trimethyl pentaphenyl trisiloxane and diphenyl dimethicone, which are component (b), were varied. In Comparative Example 11, wherein the percentage of diphenyl dimethicone was high, the separation condition was not satisfied and the sample stability was inferior.

From the above, in view of the stability, it is preferable that decamethylcyclopentasiloxane is blended in the lip cosmetic of the present invention. It is also preferable that 50 mass % or more of trimethyl pentaphenyl trisiloxane is contained in the component (b).

TABLE 6

|  | Example 11 | Reference Example |
|---|---|---|
| Glyceryl monoisostearate | 14 | 4.5 |
| Glyceryl diisostearate | — | 7.5 |
| Glyceryl triisostearate | — | 3 |
| Trimethyl pentaphenyl trisiloxane (viscosity: 165 mPa · s)※1 | 56 | 55 |
| Decamethylcyclopentasiloxane | 15 | 15 |
| Coloring material | 4 | 4 |
| Polyethylene wax | 7 | 7 |
| Ion-exchanged water | 3 | 3 |
| Dynamite glycerin | 1 | 1 |
| (2) Secondary adhesion resistance effect | A* | C |
| (3) Stability | A* | A* |

According to the reference example, wherein the composition was approximately the same as that of Example 11 except for the replacement of a portion of glyceryl monoisostearate by glyceryl diisostearate and glyceryl triisostearate, the presence of glyceryl diisostearate and glyceryl triisostearate deteriorate the secondary adhesion resistance effect.

Thus, in the lip cosmetic of the present invention, it is preferable that the sum of the blending quantities of glyceryl diisostearate and glyceryl triisostearate is preferably 10 mass % or less, relative to the total amount of the cosmetic, especially preferably 7 mass % or less, and more preferably that they are not contained.

Hereinafter, formulation examples of the lip cosmetic of the present invention will be illustrated. It is to be understood that the present invention is not limited by these formulation examples and is specified by the scope of claims.

Formulation Example 1

| Blending components | mass % |
|---|---|
| (1) Glyceryl monoisostearate (purity: 98%) | 14 |
| (2) Trimethyl pentaphenyl trisiloxane (Methyl phenyl silicone FZ3156 (manufactured by Dow Corning Toray Co., Ltd.)) | 71 |
| (3) Coloring material | 7 |
| (4) Polyethylene wax | 4 |
| (5) Ion-exchanged water | 3 |
| (6) Glycerin | 1 |

Production Method:

Components (1) to (4) were mixed at 90° C., and warmed components (5) and (6) were added and mixed. The deaeration and filling were carried out and then it was cooled.

Formulation Example 2

| Blending components | mass % |
|---|---|
| (1) Glyceryl monoisostearate (purity: 98%) | 14 |
| (2) Trimethyl pentaphenyl trisiloxane (Methyl phenyl silicone FZ3156 (manufactured by Dow Corning Toray Co., Ltd.)) | 48 |
| (3) (Alkyl acrylate/dimethicone) copolymer | 5 |
| (4) Decamethylcyclopentasiloxane | 11 |
| (5) Polyethylene wax | 9 |
| (6) Coloring material | 5 |
| (7) Ion-exchanged water | 6 |
| (8) Glycerin | 2 |

Production Method:

Components (1) to (6) were mixed at 90° C., and warmed components (7) and (8) were added and mixed. The deaeration and filling were carried out and then it was cooled.

Formulation Example 3

| Blending components | mass % |
|---|---|
| (1) Glyceryl monoisostearate (purity: 98%) | 14 |
| (2) Trimethyl pentaphenyl trisiloxane (Methyl phenyl silicone FZ3156 (manufactured by Dow Corning Toray Co., Ltd.)) | 29 |

-continued

| Blending components | mass % |
|---|---|
| (3) Dimethyl diphenyl polysiloxane (Silicone KF54 (manufactured by Shin-Etsu Chemical Co., Ltd.)) | 20 |
| (4) Stearoyl inulin | 1 |
| (5) Decamethylcyclopentasiloxane | 15 |
| (6) Polyethylene wax | 8 |
| (7) Coloring material | 5 |
| (8) Ion-exchanged water | 6 |
| (9) Glycerin | 2 |

Production Method:

Components (1) to (7) were mixed at 90° C., and warmed components (8) and (9) were added and mixed. The deaeration and filling were carried out and then it was cooled.

What is claimed is:

1. A lip cosmetic comprising the following components (a) to (d):
   (a) 4.5 to 35 mass % of glyceryl monoisostearate;
   (b) 30 to 80 mass % of one or more kinds of methyl phenyl silicones that do not separate out when mixed with (a) at 90° C. and separate out when mixed with (a) at 25° C.;
   (c) 5 mass % or more of water and/or glycerin, relative to the component (a), and 24 mass % or less, relative to the total amount of the cosmetic; and
   (d) 4 to 10 mass % of a wax, wherein the components (a) to (d) form a liquid crystal in the lip cosmetic.

2. The lip cosmetic according to claim 1, wherein component (b) contains trimethyl pentaphenyl trisiloxane.

3. The lip cosmetic according to claim 2, wherein 50 mass % or more of trimethyl pentaphenyl trisiloxane is contained in the component (b).

4. The lip cosmetic according to claim 1, wherein glyceryl diisostearate and glyceryl triisostearate are not contained or the sum of the blending quantities of them is 10 mass % or less relative to the total amount of the cosmetic.

5. The lip cosmetic according to claim 1, wherein (e) 1 to 20 mass % of a coloring material is contained.

6. The lip cosmetic according to claim 2, wherein glyceryl diisostearate and glyceryl triisostearate are not contained or the sum of the blending quantities of them is 10 mass % or less relative to the total amount of the cosmetic.

7. The lip cosmetic according to claim 3, wherein glyceryl diisostearate and glyceryl triisostearate are not contained or the sum of the blending quantities of them is 10 mass % or less relative to the total amount of the cosmetic.

8. The lip cosmetic according to claim 2, wherein (e) 1 to 20 mass % of a coloring material is contained.

9. The lip cosmetic according to claim 3, wherein (e) 1 to 20 mass % of a coloring material is contained.

10. The lip cosmetic according to claim 4, wherein (e) 1 to 20 mass % of a coloring material is contained.

11. A lip cosmetic comprising the following components (a) to (d):
    (a) 4.5 to 35 mass % of glyceryl monoisostearate;
    (b) 30 to 80 mass % of one or more kinds of methyl phenyl silicones that do not separate out when mixed with (a) at 90° C. and separate out when mixed with (a) at 25° C.;
    (c) 5 mass % or more of water and/or glycerin, relative to the component (a), and 24 mass % or less, relative to the total amount of the cosmetic; and
    (d) 4 to 10 mass % of a wax,
    wherein the components (a) to (d) form a reverse hexagonal liquid crystal in the lip cosmetic.

12. The lip cosmetic according to claim 11, wherein component (b) contains trimethyl pentaphenyl trisiloxane.

13. The lip cosmetic according to claim 12, wherein 50 mass % or more of trimethyl pentaphenyl trisiloxane is contained in the component (b).

14. The lip cosmetic according to claim 11, wherein glyceryl diisostearate and glyceryl triisostearate are not contained or the sum of the blending quantities of them is 10 mass % or less relative to the total amount of the cosmetic.

15. The lip cosmetic according to claim 11, wherein (e) 1 to 20 mass % of a coloring material is contained.

16. The lip cosmetic according to claim 12, wherein glyceryl diisostearate and glyceryl triisostearate are not contained or the sum of the blending quantities of them is 10 mass % or less relative to the total amount of the cosmetic.

17. The lip cosmetic according to claim 13, wherein glyceryl diisostearate and glyceryl triisostearate are not contained or the sum of the blending quantities of them is 10 mass % or less relative to the total amount of the cosmetic.

18. The lip cosmetic according to claim 12, wherein (e) 1 to 20 mass % of a coloring material is contained.

19. The lip cosmetic according to claim 13, wherein (e) 1 to 20 mass % of a coloring material is contained.

20. The lip cosmetic according to claim 14, wherein (e) 1 to 20 mass % of a coloring material is contained.

* * * * *